(12) United States Patent
Modestino et al.

(10) Patent No.: US 11,313,045 B2
(45) Date of Patent: Apr. 26, 2022

(54) ELECTROHYDRODIMERIZATION OF ALIPHATIC OLEFINS WITH ELECTROCHEMICAL POTENTIAL PULSES

(71) Applicant: New York University, New York, NY (US)

(72) Inventors: Miguel A. Modestino, New York, NY (US); Daniela Eugenia Blanco Jimenez, Brooklyn, NY (US)

(73) Assignee: New York University, New York, NY (US)

( * ) Notice: Subject to any disclaimer, the term of this patent is extended or adjusted under 35 U.S.C. 154(b) by 108 days.

(21) Appl. No.: 16/834,897

(22) Filed: Mar. 30, 2020

(65) Prior Publication Data
US 2020/0308716 A1 Oct. 1, 2020

Related U.S. Application Data

(60) Provisional application No. 62/827,021, filed on Mar. 30, 2019.

(51) Int. Cl.
| | |
|---|---|
| *C25B 3/29* | (2021.01) |
| *C25B 15/02* | (2021.01) |
| *C25B 9/19* | (2021.01) |
| *C07C 255/05* | (2006.01) |
| *C25B 11/043* | (2021.01) |

(52) U.S. Cl.
CPC ............... *C25B 3/295* (2021.01); *C25B 9/19* (2021.01); *C25B 15/02* (2013.01); *C07C 255/05* (2013.01); *C25B 11/043* (2021.01)

(58) Field of Classification Search
None
See application file for complete search history.

(56) References Cited

U.S. PATENT DOCUMENTS

| | | | | |
|---|---|---|---|---|
| 3,647,651 A | * | 3/1972 | Ganci | ..................... C25B 3/295 |
| | | | | 205/342 |
| 5,593,557 A | * | 1/1997 | Sopher | ..................... C25B 3/295 |
| | | | | 204/290.01 |

* cited by examiner

*Primary Examiner* — Wojciech Haske
(74) *Attorney, Agent, or Firm* — Hodgson Russ LLP

(57) ABSTRACT

Methods of making aliphatic compounds having two or more electron withdrawing groups and compositions comprising aliphatic organic compounds having one or more electron withdrawing groups. The methods are based on electrohydrodimerization of aliphatic olefinic compounds having one or more electron withdrawing groups using pulsed potential waveforms. A method may produce adiponitrile by electrolysis of acrylonitrile using pulsed waveforms. A composition may be an electrochemically produced organic phase composition. A composition may comprise one or more undesirable products, such as, for example, propionitrile, AN-derived oligomers, and the like. A composition may not have been subjected to any purification and/or separation after electrochemical production of one or more aliphatic compounds comprising two or more electron withdrawing groups.

19 Claims, 9 Drawing Sheets
(9 of 9 Drawing Sheet(s) Filed in Color)

ELECTROHYDRODIMERIZATION OF ALIPHATIC OLEFINS WITH ELECTROCHEMICAL POTENTIAL PULSES

CROSS REFERENCE TO RELATED APPLICATIONS

This application claims priority to U.S. Provisional Application No. 62/827,021, filed on Mar. 30, 2019, the disclosure of which is hereby incorporated by reference in its entirety.

FIELD OF THE DISCLOSURE

The disclosure generally relates to electrohydrodimerization of aliphatic olefins. More particularly the disclosure generally relates to electrohydrodimerization of aliphatic olefins using electrochemical potential pulses.

BACKGROUND OF THE DISCLOSURE

The electrification of the chemical industry has gained considerable relevance in the global landscape, given the possibility for easy integration of renewable energy sources that could significantly reduce global $CO_2$ emissions. Within the electrochemical industry, organic electrosynthetic processes currently account for only a small fraction of industrial processes, but continue to attract attention due to their vast potential to reduce the chemical industry's carbon footprint and access previously untapped chemical transformations with safer processes that are carried out at mild operating conditions.

The electrohydrodimerization of acrylonitrile (AN) to adiponitrile (ADN), a key intermediate to Nylon 6,6, has been considered the most successful and largest organic electrosynthesis in industry. This organic electrosynthetic process offers several advantages against the thermochemical production route, which currently holds most of the ADN global market, but uses highly toxic reactants and elevated pressure and temperature in a two-step transformation process.

The ADN electrochemical production route is a one-step chemical process that relies on more benign aqueous-based electrolytes and requires mild temperature and pressure. This reaction faces the same challenges that are common among organic electrosynthetic processes, including low reactant solubility, electrolyte stability, and selectivity control. The electrosynthesis of ADN is characterized by a complex set of reaction pathways that can lead to the formation of the desired product, ADN, or of multiple by-products (FIG. 1). Propionitrile (PN) is the most common by-product in the process, favored at high current densities that lower reactant concentrations in the electrical double layer (EDL), while 1,3,6 tricyanohexane and other higher-weight AN-derived oligomers are favored with high AN concentration in the EDL. Hydrogen is another common by-product in the system, mostly controlled by the use of cadmium and lead as cathode materials. The electrolyte composition, electrode materials, and operating conditions have been optimized in the past decades to control these side reactions, but electrochemical techniques have not yet been implemented, to the best of our knowledge, to improve control of reactant concentration next to the electrode surface and effectively mitigate mass transport limitations in the system.

Given that ADN electrosynthesis is strongly influenced by mass transport, it is critical to control reactant diffusive fluxes to the EDL in order to improve selectivity. One way that this can be achieved is by dynamically regulating the flux of electrons and thus the electrochemical reaction rates at the electrodes. Such dynamic use of electrochemical rates has been widely used for mechanistic and kinetic quantitative studies in the form of electrochemical pulsed techniques. These techniques can allow the cyclic renewal of the diffusion layer and affect the interaction of electroactive species with the reaction surface, depending on the time lengths and potential wave forms implemented. Even in non-convective systems, cyclic renewal of the EDL can be achieved with long enough base potentials that provide the time for reactant diffusive transport from the bulk to the EDL, facilitating reactant replenishment.

Pulsed techniques have been previously used for the electro-reduction of $CO_2$, finding a strong influence in product distribution due to electrode surface modifications and variations on reaction intermediate desorption energies and reactant concentration values next to the electrode surface. Moreover, pulse techniques have also shown strong influence on crystallization processes and adherence to substrate during electrochemical deposition.

Previous studies have investigated the effect of reactant bulk concentration on the product distribution of the electrohydrodimerization of AN to ADN, identifying its strong influence on reaction selectivity.

SUMMARY OF THE DISCLOSURE

The present disclosure provides methods of making aliphatic compounds comprising two or more electron withdrawing groups. The present disclosure also provides compositions comprising aliphatic compounds comprising two or more electron withdrawing groups.

In an aspect, the present disclosure provides methods of making aliphatic compounds comprising two or more electron withdrawing groups. The methods are based on electrohydrodimerization of aliphatic olefinic compounds comprising one or more electron withdrawing groups using pulsed potential waveforms. As an illustrative example, a method produces adiponitrile by electrolysis of acrylonitrile using pulsed waveforms. A method may (e.g., an electrohydrodimerization method) comprise electrolyzing a reaction mixture (e.g., a solution), where the reaction mixture, includes, but is not limited to, aliphatic olefinic compounds comprising one or more electron withdrawing groups, one or more salts, and water. The reaction mixture is in contact with a cathode that may have for a selected duration/durations a cathode potential sufficient to hydrodimerize aliphatic olefinic compounds and for selected duration/other selected durations a higher cathode potential at which the hydrodimerization of the aliphatic olefinic compounds either occurs at a slower rate or is completely suppressed.

In an aspect, the present disclosure provides compositions comprising aliphatic compounds comprising two or more electron withdrawing groups. A composition may be produced by a method of the present disclosure. A composition may be an electrochemically produced organic phase composition. A composition (e.g., an electrochemically produced organic phase composition) may comprise: one or more aliphatic compound comprising two or more electron withdrawing groups (e.g., adiponitrile) at a concentration of 1 to 70 wt % (based on the total weight of the composition), including all 0.1 weight percent values and ranges therebetween; one or more aliphatic olefinic compound comprising one or more electron withdrawing group (e.g., acrylonitrile) at a concentration of 0 to 85 wt % (based on the total weight of the composition), including all 0.1 weight percent values and ranges therebetween. A composition may comprise one or more undesirable products (e.g., propionitrile, AN-derived oligomers, such as for example, 1,3,6-tricyanohexane, and the like, and the like, or a combination thereof) at a concentration of 0 to 30 wt % (based on the total weight of the composition), including all 0.1 weight percent values and ranges therebetween. A composition may not have been subjected to any purification and/or separation (e.g., removal of the one or more aliphatic compound comprising two or more electron withdrawing groups (e.g., adiponitrile) and/or one or more aliphatic olefinic compound comprising one or more electron withdrawing group (e.g., acrylonitrile) and/or or undesirable products) after electrochemical production of the adiponitrile.

BRIEF DESCRIPTION OF THE FIGURES

The patent or application file contains at least one drawing executed in color. Copies of this patent or patent application publication with color drawing(s) will be provided by the Office upon request and payment of the necessary fee.

For a fuller understanding of the nature and objects of the disclosure, reference should be made to the following detailed description taken in conjunction with the accompanying figures.

DETAILED DESCRIPTION OF THE DISCLOSURE

Figure 1:
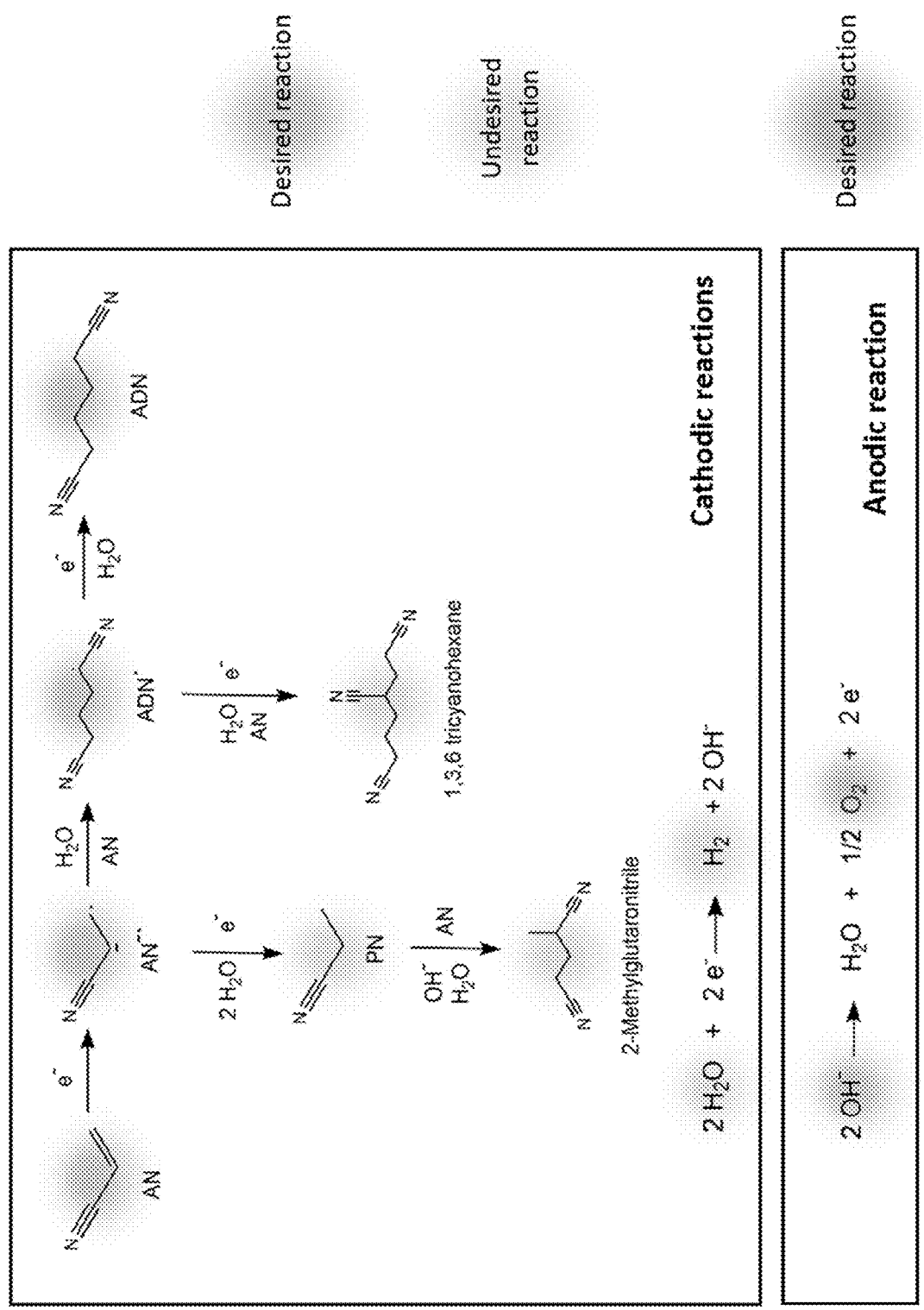
FIG. 1 shows an example of reaction pathways for the electrohydrodimerization of acrylonitrile to adiponitrile, including anodic reaction and cathodic side reactions.

Although subject matter of the present disclosure is described in terms of certain embodiments and examples, other embodiments and examples, including embodiments and examples that do not provide all of the benefits and features set forth herein, are also within the scope of this disclosure. For example, various structural, logical, process step, and electronic changes may be made without departing from the scope of the disclosure.

Ranges of values are disclosed herein. The ranges set out a lower limit value and an upper limit value. Unless otherwise stated, the ranges include the lower limit value, the upper limit value, and all values between the lower limit value and the upper limit value, including, but not limited to, all values to the magnitude of the smallest value (either the lower limit value or the upper limit value).

As used herein, unless otherwise indicated, the term "group" refers to a chemical entity that is monovalent (i.e., has one terminus that can be covalently bonded to other chemical species), divalent, or polyvalent (i.e., has two or more termini that can be covalently bonded to other chemical species). The term "group" also includes radicals (e.g., monovalent radicals and multivalent radicals, such as, for example, divalent radicals, trivalent radicals, and the like). Examples of groups include, but are not limited to:

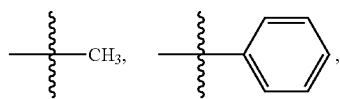

-continued

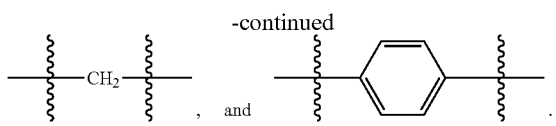

As used herein, unless otherwise indicated, the term "alkyl group" refers to branched or unbranched saturated hydrocarbon groups. Examples of alkyl groups include, but are not limited to, methyl groups, ethyl groups, propyl groups, butyl groups, isopropyl groups, tert-butyl groups, and the like. In various examples, the alkyl group is a $C_1$ to $C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) group. The alkyl group can be unsubstituted or substituted with one or more substituent. Examples of substituents include, but are not limited to, various substituents such as, for example, halogens (—F, —Cl, —Br, and —I), aliphatic groups (e.g., alkyl groups, alkenyl groups, and alkynyl groups), aryl groups, alkoxide groups, carboxylate groups, carboxylic acids, ether groups, and the like, and combinations thereof.

As used herein, unless otherwise indicated, the term "aliphatic" refers to branched or unbranched hydrocarbon groups that, optionally, contain one or more degrees of unsaturation. Degrees of unsaturation include, but are not limited to, alkenyl groups, alkynyl groups, and cyclic aliphatic groups. In various examples, the aliphatic group is a $C_1$ to $C_{28}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, or $C_{28}$) aliphatic group. The aliphatic group can be unsubstituted or substituted with one or more substituent. Examples of substituents include, but are not limited to, halogens (—F, —Cl, —Br, and —I), aliphatic groups (e.g., alkyl groups, alkenyl groups, alkynyl groups, and the like), halogenated aliphatic groups (e.g., trifluoromethyl group), aryl groups, halogenated aryl groups, alkoxide groups, amine groups, nitro groups, carboxylate groups, carboxylic acids, ether groups, alcohol groups, alkyne groups (e.g., acetylenyl groups and the like), and the like, and combinations thereof.

The present disclosure provides methods of making aliphatic compounds comprising two or more electron withdrawing groups. The present disclosure also provides compositions comprising aliphatic compounds comprising two or more electron withdrawing groups.

In an aspect, the present disclosure provides methods of making aliphatic compounds comprising two or more electron withdrawing groups. The methods are based on electrohydrodimerization of aliphatic olefinic compounds comprising one or more electron withdrawing groups using pulsed potential waveforms. Non-limiting examples of the methods are described in the Statements and Examples provided herein.

As an illustrative example, a method produces adiponitrile by electrolysis of acrylonitrile using pulsed waveforms. A non-limiting example of a pathway for the electrohydrodimerization of acrylonitrile to adiponitrile, including anodic reaction and cathodic side reactions is shown in FIG. 1.

A method may (e.g., an electrohydrodimerization method) comprise electrolyzing a reaction mixture (e.g., a solution), where the reaction mixture, includes, but is not limited to, aliphatic olefinic compounds comprising one or more electron withdrawing groups, one or more salts, and water. The reaction mixture is in contact with a cathode. The cathode may have for a selected duration/durations a cathode potential sufficient to hydrodimerize aliphatic olefinic compounds and for selected duration/other selected durations a higher cathode potential at which the hydrodimerization of the aliphatic olefinic compounds either occurs at a slower rate or is completely suppressed. The electrolysis is carried out using a pulsed potential waveform applied to the cathode. A product of the method, which may be referred to as a hydrodimerization product, is a one or more aliphatic compound comprising two or more electron withdrawing groups.

A reaction mixture may have various pH. The pH level may be the same (e.g., held constant) during the reaction or change during the reaction. A reaction mixture may have at least an initial pH of 7 to 13, including all 0.1 pH values and ranges therebetween. In the case of adiponitrile, it may be desirable to use a pH of 9-13.

Various aliphatic olefinic compounds can be used in the methods. Combinations of aliphatic olefinic compounds may be used. Aliphatic olefinic compounds comprise one or more electron withdrawing groups. Non-limiting examples of electron withdrawing groups include —CN, —CF$_3$, carboxylic acids/carboxylates, esters, amides, phosphonates, phosphinates, phosphine oxides, sulfones, pyridines (e.g., 2-pyridines, 4-pyridines), and the like, and combinations thereof. The aliphatic olefinic compound may be a $C_1$ to $C_{14}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, or $C_{14}$), including all integer number of carbons and ranges therebetween, aliphatic olefinic compound and may have one or more terminal or internal carbon-carbon double bond.

Non-limiting examples of aliphatic olefinic compounds comprising one or more electron withdrawing groups include aliphatic alpha, beta-olefinic compounds, such as, for example aliphatic alpha, beta-olefinic compounds having the following structure:

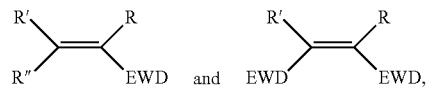

where EWD is an electron withdrawing group and R, R', and R" are independently chosen from hydrogen and organic substituents.

Non-limiting examples of suitable aliphatic olefinic compounds have the following structure:

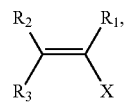

where X corresponds to an electron withdrawing group and $R_1$, $R_2$, and $R_3$ are, independently, chosen from hydrogen and organic substituents. In the case of these aliphatic olefinic compounds, the product of the method would have the following structure:

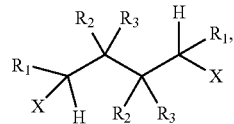

where X, $R_1$, $R_2$, and $R_3$ correspond to $R_1$, $R_2$, and $R_3$ described for the aliphatic olefinic compounds. Non-limiting examples of organic substituents include alkyl groups.

Examples of aliphatic olefinic compounds comprising one or more electron withdrawing groups include, but are not limited to, acrylonitrile, ethyl acrylate, acrylamide, and the like, and combinations thereof.

A product may be an aliphatic compound comprising two or more electron withdrawing groups. The aliphatic compound may be a $C_1$ to $C_{28}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$), including all integer number of carbons and ranges therebetween, aliphatic compound. Examples of products include, but are not limited to, adiponitrile, diethyl adipate, adipamide, and the like, and combinations thereof.

Various pulsed waveforms may be used for the potential applied to the cathode (with respect to the reference electrode)—for example, pulsing from a base potential to a cathodic potential (and optionally, back). A waveform may comprise one or more pulses. A method may comprise applying a potential with a waveform having a plurality of pulses having the same base potential, the same cathodic potential, the same resting duration, the same cathodic potential, or any combinations thereof. For example, for individual pulses, the base potential may be the same as all the other pulses or may be different than one or more of the other pulses. A waveform may comprise two or more different pulses (e.g., having different base and/or cathodic potentials and/or durations). An individual pulse may have a cathodic potential of 0V to −4V (e.g., measured against a reference electrode, such as, for example, a Ag/AgCl reference electrode). The cathodic potential may be constant or vary for at least a portion or all of the cathodic duration. For example, the cathodic potential is in the form of a sine wave, a square wave, a triangle wave, a saw-tooth wave, and the like. Similarly, the base potential may be constant or vary for at least a portion or all of the resting duration. For example, the base potential is in the form of a sine wave, a square wave, a triangle wave, a saw-tooth wave, and the like.

A method may be carried out at various pHs and/or temperatures. A method may be carried out a pH 7 to 13, including all 0.1 pH values and ranges therebetween, and/or a temperature of 20-60° C., including all integer ° C. values and ranges therebetween.

Various reaction mixtures can be used. A reaction mixture comprises AN in aqueous electrolyte that includes, but is not limited to, one or more phosphate and/or one or more buffer salt, EDTA, and one or more quaternary ammonium salt. In an example, a reaction mixture comprises AN (e.g., 3-30 wt %, (based on the total weight of the reaction mixture)) in aqueous electrolyte that includes, but is not limited to, phosphate(s) or buffer salt(s) (e.g., 5-15 wt % (based on the total weight of the reaction mixture)), EDTA (e.g., 0.5-3 wt % (based on the total weight of the reaction mixture)) and quaternary ammonium salt(s) (0.1-6 wt % (based on the total weight of the reaction mixture)).

A method may be carried out in a batch mode (e.g., using a closed system). A method may be carried out in a continuous/semi-continuous mode (e.g., using a flow system).

Without intending to be bound by any particular theory, it is considered that a method of the present disclosure produces more aliphatic compounds comprising two or more electron withdrawing groups (e.g., adiponitrile) relative to the same method carried out using DC electrolysis. A method of the present disclosure may produce 20% or more, 30% or more, 40% or more, 50% or more, 60% or more, 70% or more, 80% or more, 90% or more, or 100%, aliphatic compounds comprising two or more electron withdrawing groups (e.g., adiponitrile) relative to the same method carried out using DC electrolysis.

A method may provide desirable product production rate and/or selectivity. The product production rate of a method may be at least 10%, at least 20%, at least 30%, at least 40%, at least 50%, at least 75%, or 100% greater relative to the same method carried out using DC electrolysis and/or a method may result in at least 10%, at least 20%, at least 30%, at least 40%, at least 50%, at least 75%, or 100% reduction in one or more undesirable products relative to the same method carried out using DC electrolysis.

In an aspect, the present disclosure provides compositions comprising aliphatic compounds comprising two or more electron withdrawing groups. A composition may be produced by a method of the present disclosure. A composition may be an electrochemically produced organic phase composition. The aliphatic compounds may be a $C_1$ to $C_{28}$, including all integer number of carbons and ranges therebetween, aliphatic compound.

A composition (e.g., an electrochemically produced organic phase composition) comprising: one or more aliphatic compound comprising two or more electron withdrawing groups (e.g., adiponitrile) at a concentration of 1 to 70 wt % (based on the total weight of the composition), including all 0.1 weight percent values and ranges therebetween; one or more aliphatic olefinic compound comprising one or more electron withdrawing group (e.g., acrylonitrile) at a concentration of 0 to 85 wt % (based on the total weight of the composition), including all 0.1 weight percent values and ranges therebetween. A composition may comprise one or more undesirable products (e.g., propionitrile, AN-derived oligomers, such as for example, 1,3,6-tricyanohexane, and the like, and the like, or a combination thereof) at a concentration of 0 to 30 wt % (based on the total weight of the composition), including all 0.1 weight percent values and ranges therebetween. A composition may not have been subjected to any purification and/or separation (e.g., removal of the one or more aliphatic compound comprising two or more electron withdrawing groups (e.g., adiponitrile) and/or one or more aliphatic olefinic compound comprising one or more electron withdrawing group (e.g., acrylonitrile) and/or or undesirable products) after electrochemical production of the adiponitrile.

A composition may comprise one or more undesirable products (e.g., propionitrile, AN-derived oligomers, such as, for example, 1,3,6-tricyanohexane and the like, and the like, or a combination thereof) at a concentration of less than 30 wt %, less than 25 wt. %, less than 20 wt. %, or less than 15 wt. % (based on the total weight of the composition), where composition has not been subjected to any separation (e.g., removal of adiponitrile and/or acrylonitrile and/or undesirable products) after electrochemical production of the aliphatic compound having two more electron withdrawing groups (e.g., a product such as, for example, adiponitrile). These examples of undesirable products are those related to electrohydrodimerization of acrylonitrile to produce adiponitrile. One skilled in the art would recognize undesirable products that may result from electrohydrodimerization of other aliphatic olefinic compounds comprising one or more electron withdrawing group.

The steps of the method described in the various embodiments and examples disclosed herein are sufficient to carry out the methods of the present disclosure. Thus, in an example, a method consists essentially of a combination of the steps of the methods disclosed herein. In another embodiment, a method consists of such steps.

The following Statements provide examples of methods of the present disclosure:

Statement 1. A method of the present disclosure (e.g., a method (e.g., an electrohydrodimerization method) for making a product (e.g., one or more aliphatic compound comprising two or more electron withdrawing groups, such as, for example, adiponitrile) comprising: electrolyzing a reaction mixture (e.g., a solution) comprising: one or more aliphatic olefinic compound comprising one or more electron withdrawing group (e.g., acrylonitrile); one or more salts; and water; where the reaction mixture has at least an initial pH of 7 to 13, where the reaction mixture is in contact with a cathode (e.g., a cathode having for selected duration at least one cathode potential sufficient to hydrodimerize the one or more aliphatic olefinic compound comprising one or more electron withdrawing group (e.g., acrylonitrile) and for at least one other selected duration a higher cathode potential at which the hydrodimerization of the one or more aliphatic olefinic compound comprising one or more electron withdrawing group (e.g., acrylonitrile) either occurs at a slower rate or is completely suppressed), and the electrolysis is carried out using a pulsed potential waveform applied to the cathode, and where the product is a hydrodimer of the one or more aliphatic olefinic compound comprising one or more electron withdrawing group). The method may be carried out in a batch mode (e.g., a closed system) or a continuous/semi-continuous mode (e.g., a flow system).

Statement 2. A method according to Statement 1, where the pulsed potential waveform has a base (resting) potential (e.g., selected within a range where no faradaic reaction occurs or occurs at a lower rate than during the cathodic potential) and at least one cathodic (pulse) potential (in each case, potential is measured with respect to another electrode (e.g., an anode or reference electrode).

Statement 3. A method according to Statement 2, where the base potential is applied for a resting duration of less than 50 ms (e.g., from 0.1 ms to 50 ms, inclusive, or between 0.1 ms to 50 ms, inclusive) and the cathodic potential is applied for a cathodic duration of from 5 ms to 2000 ms (e.g., between 5 ms and 2000 ms, inclusive).

Statement 4. A method according to Statement 2 or 3, where the pulsed potential waveform alternates between the base potential and the cathodic potential.

Statement 5. A method according to any one of Statements 2-4, where each instance of base potential has a same potential value as each other instance of the base potential and/or each instance of the cathodic potential has a same potential value as each other instance of the cathodic potential.

Statement 6. A method according to any one of Statements 3-5, where each resting duration is the same as each other resting duration and/or each cathodic duration is the same as each other cathodic duration.

Statement 7. A method according to any one of Statements 2-6, where each base potential is the same or varies in the range of 0 V to −4 V (e.g., between 0 V and −4 V) measured against a Ag/AgCl reference electrode, inclusive, and/or the cathodic potential is equal to or lower than (i.e., more negative than) −2 V (e.g., measured against, for example, a Ag/AgCl reference electrode) and may vary throughout the electrolysis. A desirable production rate, for example, of adiponitrile (electrohydrodimerizing acrylonitrile), was achieved using 0V base potential and −3.5 V vs Ag/AgCl cathodic potential, −1.5 V base potential and −3.5 V vs Ag/AgCl cathodic potential, and −2.5 V base potential and −3.5 V vs Ag/AgCl cathodic potential.

Statement 8. A method according to any one of Statements 2-7, where the base potential of a pulse is constant throughout the resting duration and/or the cathodic potential of a pulse is constant throughout the cathodic duration.

Statement 9. A method according to any one of Statements 2-8, where the base potential of a pulse varies during the resting duration and/or the cathodic potential of a pulse varies during the cathodic duration.

Statement 10. A method according to Statement 9, where the base potential of a pulse varies (e.g., as a sine wave, a square wave, triangle wave, a saw-tooth wave, ramp up, ramp down, etc.) during the resting duration and/or the cathodic potential of a pulse varies (e.g., as a sine wave, a square wave, triangle wave, a saw-tooth wave, ramp up, ramp down, etc.) during the cathodic duration.

Statement 11. A method of any one of the preceding Statements, where the one or more aliphatic olefinic compound (e.g., acrylonitrile) is at least initially present in the reaction at a concentration of 3 to 30 wt % (based on the total weight of the reaction mixture), including all 0.1 weight percent values and ranges therebetween. Desirable production rates of adiponitrile (electrohydrodimerizing acrylonitrile) was achieved using acrylonitrile at least initially present at 3-5 wt % (based on the total weight of the reaction mixture).

Statement 12. A method of any one of the preceding Statements, where the one or more salts are chosen from buffer salts (e.g., sodium phosphate salts, potassium phosphate salts, and the like), EDTA, chelating agents, ion-orienting quaternary ammonium salts (e.g. tetramethylammonium hydroxide, tetraethylammonium hydroxide, tetrabutylammonium hydroxide), and the like. The one or more salts may be in the form of an aqueous buffer, such as, for example, an aqueous phosphate buffer.

Statement 13. A method of any one of the preceding Statements, where the one or more salts are at least initially present in the reaction at a concentration of 0.1 to 15 wt % (based on the total weight of the reaction mixture), including all 0.1 wt % values and ranges therebetween. A desirable production rate of adiponitrile (dimerizing acrylonitrile) was achieved using 5-10 wt % phosphates or buffer salts, 0.5-1.5 wt % (based on the total weight of the reaction mixture) EDTA, and 0.1-1 wt % (based on the total weight of the reaction mixture) quaternary ammonium salt.

Statement 14. A method of any one of the preceding Statements, where the acrylonitrile concentration and/or salt concentration and/or pH is constant or changes as a function of time.

Statement 15. A method of any one of the preceding Statements, where the electrolysis is carried out in an electrochemical cell (which may be a single compartment cell or a divided electrochemical cell) comprising the cathode. The electrochemical cell may be a static cell or flow cell.

Statement 16. A method of any one of the preceding Statements, where the electrochemical cell further comprises a metal anode (e.g., an anode comprising nickel, carbon steel, a platinum iridium-based dimensionally stable anode material, or the like) and, optionally, a reference electrode.

Statement 17. A method of any one of the preceding Statements, where the electrochemical cell further comprises a separator (e.g., a cation-exchange, anion-exchange, or bipolar membrane separating a cathode half-cell and an anode half-cell which are in electrical contact).

Statement 18. A method of any one of the preceding Statements, where the cathode has an electrochemically available surface (e.g., an exterior surface) comprising a metal (e.g., cadmium, lead, stainless steel, palladium, or an alloy thereof, and the like), carbon, or a combination thereof.

Statement 19. A method of any one of the preceding Statements, further comprising separation at least a portion of, substantially all, or all of the adiponitrile from the reaction mixture. Illustrative, non-limiting examples of separation methods include distillation, liquid-liquid decantation to separate the aqueous from the organic phase, and the like.

Statement 20. A method of any one of the preceding Statements, further comprising varying the amount of the one or more aliphatic compound comprising two or more electron withdrawing group (e.g., adiponitrile) and/or undesirable products (e.g., propionitrile, AN-derived oligomers, such as for example, 1,3,6-tricyanohexane, 2-methylglutaronitrile, and the like) produced by adjusting one or more of: i) concentration of acrylonitrile, ii) concentration of one or more salt, iii) pH, or iv) temperature.

Statement 21. A composition of the present disclosure (e.g., a composition (e.g., an electrochemically produced organic phase composition) comprising: one or more aliphatic compound comprising two or more electron withdrawing groups (e.g., adiponitrile), which may be a product, at a concentration of 1 to 70 wt % (based on the total weight of the composition), including all 0.1 weight percent values and ranges therebetween; one or more aliphatic olefinic compound (e.g., acrylonitrile) at a concentration of 0 to 85 wt % (based on the total weight of the composition), including all 0.1 weight percent values and ranges therebetween; and undesirable products (e.g., propionitrile, AN-derived oligomers, such as for example, 1,3,6-tricyanohexane and the like, and the like, or a combination thereof) at a concentration of 0 to 30 wt % (based on the total weight of the composition), including all 0.1 weight percent values and ranges therebetween, where the electrochemically produced composition has not been subjected to any separation (e.g., removal of adiponitrile and/or acrylonitrile and/or or undesirable products)) after electrochemical production of the adiponitrile)).

The following example is presented to illustrate the present disclosure. It is not intended to be limiting in any matter.

EXAMPLE 1

This example provides a description of methods and compositions of the present disclosure.

The electrohydrodimerization of acrylonitrile (AN) to adiponitrile (ADN) is a key step in the electrochemical production route for Nylon 6,6. This chemical transformation faces many challenges, common among organic electrosynthetic processes, including a complex set of desired and undesired reactions at the cathodic surface, which lowers selectivity towards ADN when mass transport limitations become significant at high reaction rates. This work investigates the effect of electrochemical pulsed potential techniques on the composition of the EDL and interaction of molecules with the electrode surface, showing the possibility to effectively tune product distribution, surpassing a 3-fold increase in ADN:PN production ratio in several cases. Furthermore, optimized combinations of these parameters have also led to a 20% increase in ADN production with a 6% reduction in energy input. The experimental data collected for this model reaction was used to train an ANN that predicts ADN production based on cathodic and resting times applied, elucidating the potential of these powerful machine learning tools to understand nano-scale processes and optimize operation conditions that maximize performance in organic electrosynthesis.

Figure 2:
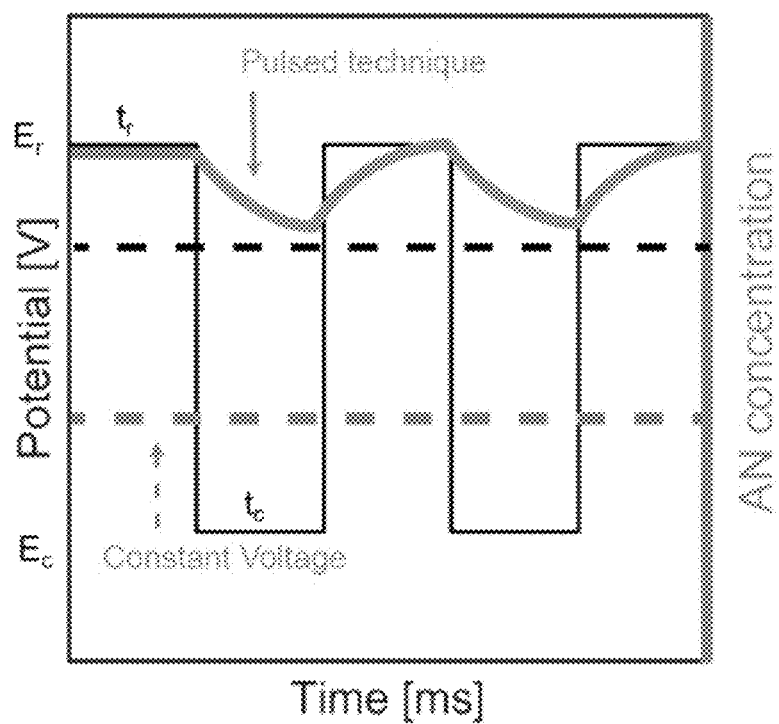
FIG. 2 shows an example of a pulse potential waveform showing the resting potential ($E_r$), cathodic potential ($E_c$), resting time ($t_r$), and cathodic time ($t_c$) under constant (black dotted lines) and pulsed voltage conditions (black solid lines). The blue lines represent the expected reactant concentration next to the electrode surface for constant (dotted) and pulsed (solid) voltage.

Pulsed electrolysis principles were used for the first time on the largest organic electrosynthetic reaction in industry, as a model reaction for organic electrosynthetic processes, to understand, for example, the effect of nanoscale diffusive processes that determine reactant concentration profiles next to the electrode surface and their influence on the product distribution. The present study implements differential pulse amperometry (DPA) techniques to understand the effect of diffusion-based reactant concentration regeneration in the EDL. Among other pulsed techniques, DPA applies pulsed potential wave forms with constant base potential and pulse potential values. The base or resting potential value is commonly selected within the range where no faradaic reaction occurs, allowing the diffusion of electroactive species from the bulk to the electrode surface during resting times to mitigate mass transport limitations and control PN formation. FIG. 2 describes the expected effect of the potential wave form on reactant concentration next to the electrode surface, and the main operation parameters studied.

Experimental. Materials. All chemicals used were acquired from Sigma-Aldrich, including sodium phosphate, tetrabutylammonium (TBA) hydroxide, ethylenediaminetetraacetic acid (EDTA) disodium salt, and acrylonitrile. A fresh aqueous catholyte solution with 0.5 M (8 wt %) sodium phosphate, 0.03 M (1 wt %) EDTA, and 0.02 M (0.5 wt %) TBA hydroxide was prepared before adding 0.6 M (3 wt %) AN for each experiment. A 1M sulfuric acid was used as anolyte, and diffusion through the membrane was assumed negligible given that the cathodic chamber pH remained constant throughout the experiments A 1 $cm^2$ cadmium foil (American Elements) working electrode, a platinum mesh (Alfa Aesar) counter electrode, and a Ag/AgCl (4 M KCl) reference electrode were used for all experiments.

Figure 3:
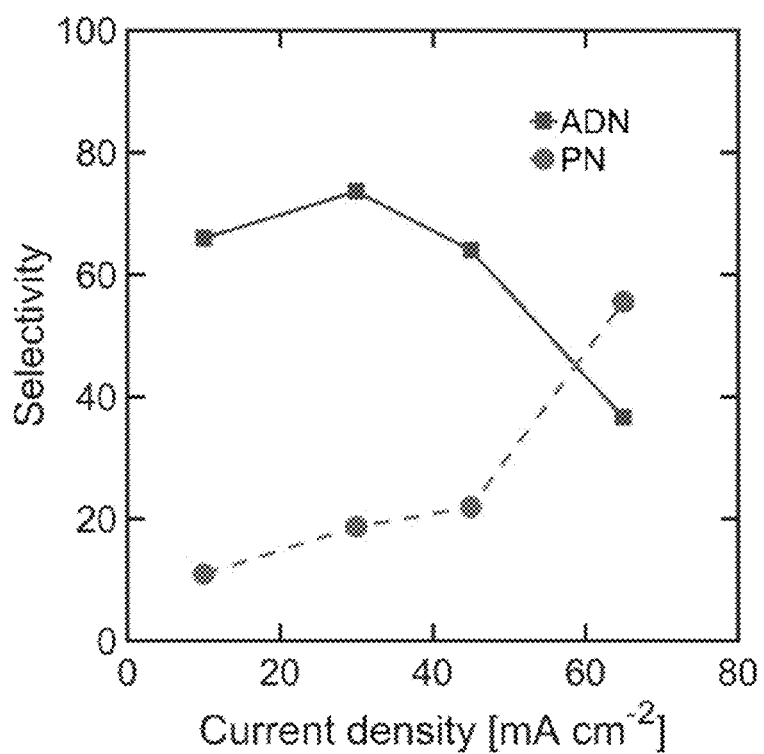
FIG. 3 shows a comparative example showing ADN and PN selectivity at varying current densities under DC operation conditions.

Electrochemical characterization. A 3-electrode setup was used to study the effect of pulsed potential techniques on the diffusion layer and the cathodic half-cell reactions. Chronoamperometry (CA) and DPA techniques were performed for 20 minutes using a BioLogic VSP-300 potentiostat. FIG. 3 shows the H-cell fabricated with VeroClear Polyjet resin in a Stratasys Object30 Pro additive manufacturing tool. A Nafion N117 membrane, sealed between two viton gaskets, separated the two chambers, avoiding the deposition of metal ions from the anode on the cathode surface. Prior to experiments, the cadmium electrode surface was operated at 40 mA $cm^{-2}$ for 10-12 hours with the catholyte solution. A constant electrolyte volume of 8 mL was vigorously stirred (700 rpm and a 1.2 cm long stirring bar) in all experiments, temperature was maintained at 25° C. using a hot plate and a sand bath, and electrolyte pH was measured and kept at 11 with a B30PCI pH meter from VWR.

Chemical Analysis. The organic compounds were separated from the aqueous electrolyte via liquid-liquid extraction with toluene. The organic phase was then analyzed in a Shimadzu gas chromatographer equipped with a mass spectrometer GCMS-QP2010 and an Agilent 7890B gas chromatographer and 5977B mass spectrometer. Component identification and quantification were performed using continuously updated calibration curves for AN, PN, and ADN.

Mass Transport Model. Time-dependent reactant consumption next to the electrode surface was studied using Matlab®, assuming diffusion-based reactant mass transport from the bulk electrolyte to the electrode surface in a one-dimensional model. Finite difference approximations were used to solve differential mass transport equations following Fick's law. Applied current density values were correlated to the reactant consumption rate using Faraday's law and square-wave potential waveforms were implemented to simulate pulsed-potential techniques.

Artificial Neural Network Simulation. A feed-forward artificial neural network (ANN), consisting of 2 layers with 10 neurons each, was built and trained with 26 experimental data points, using resting and cathodic times as inputs to predict ADN production rates. Levenberg-Marquardt algorithm was used as training function and mean squad error for performance evaluation. Experimental data was collected with −3.5 V vs Ag/AgCl cathodic potential and 0 V vs Ag/AgCl resting potential. Average mean error of the prediction was calculated using 20 points for network training and 6 points for error calculation.

Results. DC operation (comparative example). Product distribution of the electrohydrodimerization of AN to ADN is expected to strongly depend on the current density implemented, as it determines the reaction rate and system limitations at a given reactant bulk concentration. FIG. 3 summarizes the changes observed in selectivity towards ADN and PN at varying current densities under constant (DC) operation. The increased PN production found at higher current densities suggests the presence of mass transport limitations, discussed on previous studies, as higher AN consumption rates may lead to lower reactant concentrations in the EDL, favoring the formation of the by-product that requires only one AN molecule. In this way, the careful control of applied current densities can help maximize ADN production while limiting PN formation, suggesting that the control of reactant concentration in the EDL could help further improve the production rate of desired products.

Figure 4:
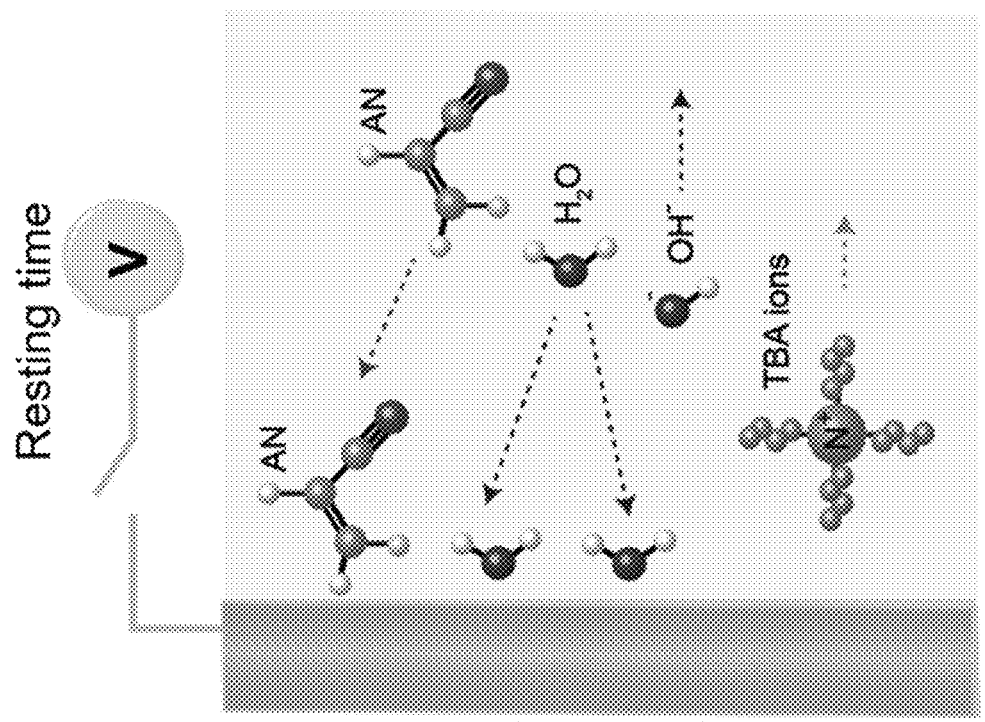
FIG. 4 shows a graphical description of the effects that cathodic and resting potentials can have on the system. During cathodic times, the faradaic reduction of AN to ADN takes place, TBA ions are electrostatically attracted to the electrode surface, and hydroxyl ions migrate to the anode to preserve charge neutrality. When no potential is applied during resting times, reactant molecules can diffuse from the bulk to the EDL and TBA ions are not electrostatically attracted to the electrode surface, which could allow a higher water coverage of the electrode surface and affect molecule solvation.
Figure 4:
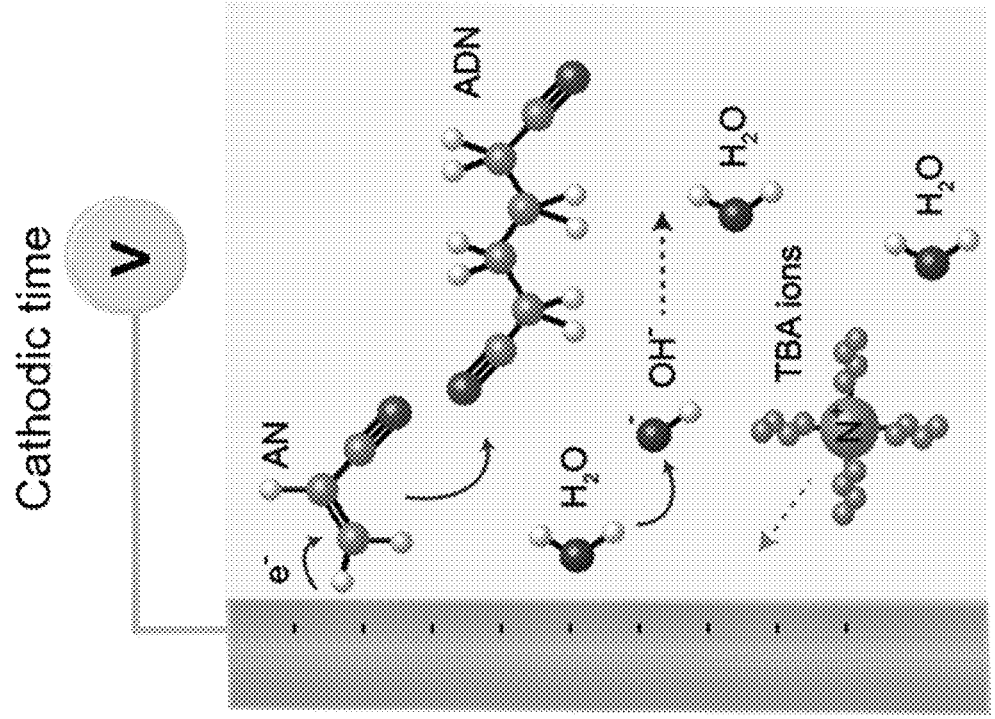

Effect of resting and cathodic time. The effect of electrochemical pulses in the EDL can go beyond AN concentration profiles. During cathodic times, the working electrode is charged negatively, and electrons flow according to reaction kinetics, consuming AN to produce ADN and by-products. In addition, charged species migrate according to the existing electric field, maintaining an electrically neutral system. During cathodic times (FIG. 4), TBA and sodium ions experience electrostatic attraction to the negatively charged electrode and hydroxyl ions migrate towards the anode to preserve charge neutrality. The presence of TBA ions in the EDL can help increase AN concentration next to the electrode surface, given the higher affinity that long alkyl chains have towards organic molecules, while also expelling water molecules from the EDL.

On the other hand, the negatively charged working electrode will gradually lose its charge during resting times, giving rise to non-faradaic currents and affecting the concentration profile of species in the EDL. When no potential is applied to the system during resting times (FIG. 4), no faradaic reaction takes place and reactant molecules can diffuse from the bulk, allowing the replenishment of reactant concentration next to the electrode surface. At the same time, TBA and positively charges ions are not attracted electrostatically by the electrode, and if their presence in the EDL varies, the water coverage of the electrode surface and the solvation of molecules will also be affected. This can further influence hydrogen evolution rates and the stabilization of different intermediate species that could favor undesired reaction pathways.

Figure 5:
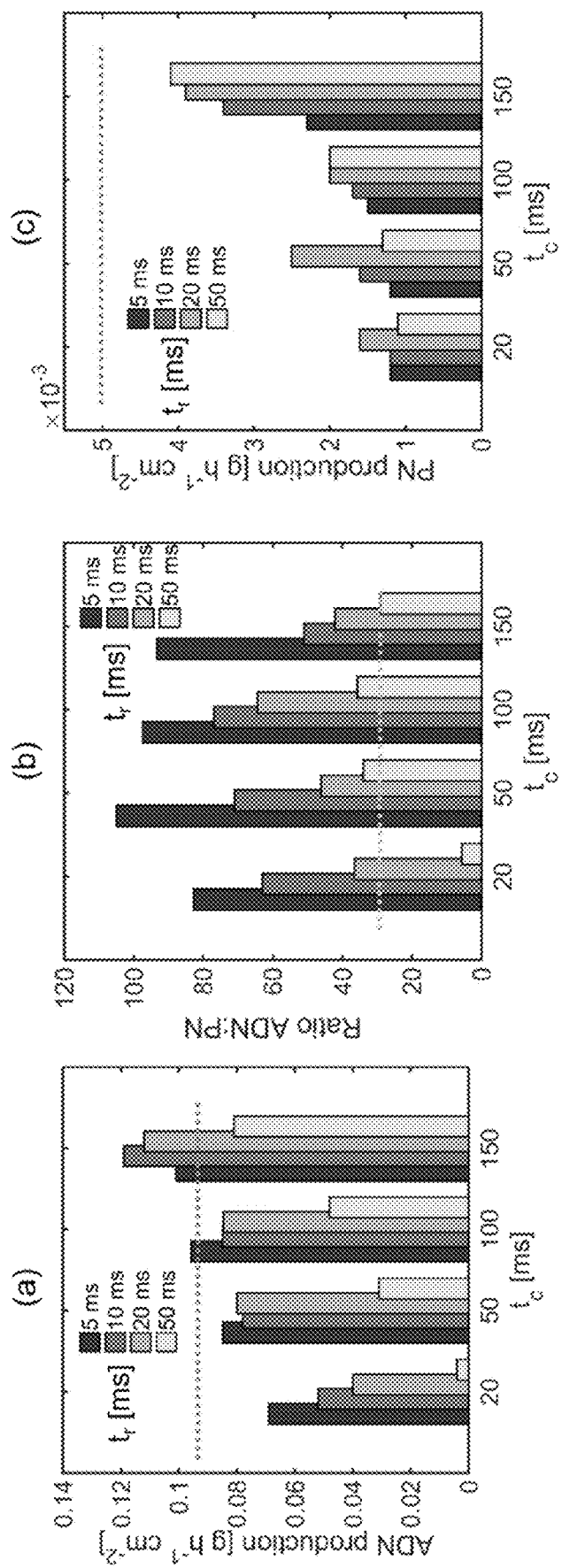
FIG. 5 shows (a) ADN production rate, (b) ratio ADN:PN production and (c) PN production rate at −3.5 V (V=volt(s)) cathodic potential and 0 V vs Ag/AgCl resting potential for various $t_c$ and $t_r$ combinations with <3% standard deviation. The dotted lines represent the ADN:PN ratio and PN production obtained under constant operation at −3.5 V. Moving from left to right on the $t_c$ axis, the values for each of the four $t_c$ times corresponds to a $t_r$ of 5 ms, 10 ms, 20 ms, and 50 ms (ms=millisecond(s)).

Resting and cathodic times can thus affect molecule solvation and the concentration profile of reactant and other electrolyte species in the EDL, determining the extent of mass transport limitations in the system and influencing product distribution. FIG. 5 shows the effect of cathodic ($t_c$) and resting ($t_r$) times on (a) ADN production rate, (b) production ratio of ADN with respect to PN, and (c) PN production rate for a cathodic potential of −3.5 V vs Ag/AgCl and a resting potential of 0 V vs Ag/AgCl. The cathodic potential of −3.5 V vs Ag/AgCl corresponds to approximately −60 mA cm$^{-2}$, based on the corresponding current density under DC operation. Product distribution is studied in terms of production rate given that the accurate calculation of faradaic reaction and non-faradaic transient currents with pulsed potential techniques was not possible with the computer power available for such short time frames, impeding the reliable report of faradaic efficiencies. In the same way, the effect of non-faradaic currents is not considered in the modelling of species mass transport.

The experimental results displayed in FIG. 5 show significant variations on ADN:PN ratio and production rates for both species when potential pulses of changing duration are implemented. In most cases, the ratio of desired to undesired product is higher than that obtained under chronoamperometric operation (dotted line), and the increase on ADN:PN ratio is mostly due to the reduction in PN production (See FIGS. 5 (a) and (c)). This suggests that mass transport limitations, which are expected at −3.5 V vs Ag/AgCl electrode potential, are being mitigated with the periodic regeneration of reactant concentration next to the electrode surface, limiting PN formation.

The effect that pulsed potential techniques can have on reactant concentration is expected to be very strong next to the electrode surface. The simulated time-dependent variations in reactant concentration at the electrode surface under chronoamperometric and pulsed potential operation conditions are presented in FIG. 6. The mass transport model shows how reactant concentration at the electrode surface can be regenerated to a certain extent during resting times through diffusion-based transport from the bulk. Complete renewal of the diffusion layer is not achieved with the time frames used in the experiments, but higher reactant concentrations are maintained when pulsed techniques are implemented. Although the modified reactant concentration profile can help explain the observed reduction of PN production with pulsed potential techniques, it does not necessarily explain all trends observed for the different combinations of resting and cathodic times.

FIG. 5 (a) shows the effect of cathodic and resting times on the ADN production rate. ADN production decreases with longer resting times, even if higher reactant concentrations are expected next to the electrode surface (FIG. 6 (a)). This suggests that higher reactant concentrations can help effectively mitigate PN formation but do not necessarily favor ADN formation. Cathodic times have an opposite effect on ADN production but support the previous statement. As observed in FIG. 5 (a), ADN production is increased with higher cathodic times, even if these lead to lower reactant concentrations (FIG. 6 (b)).

The trend observed suggests that ADN production is limited by overall cathodic reaction times, which are reduced with higher $t_r$ and lower $t_c$. Furthermore, lower overall cathodic times can also lead to accumulation of AN in the EDL, which could facilitate the self-polymerization reactions and oligomer formation, while limiting ADN production. These undesired species are not quantified on the results presented as they are not easily analyzed in GCMS systems due to their high molecular weight.

The combination of resting and cathodic times can also influence PN production rates, as displayed on FIG. 5 (c). Longer resting times are expected to limit PN formation, given that AN concentrations are expected to be higher in the EDL thus helping mitigate mass transport limitations. Although PN formation is controlled with pulsed potentials when compared to DC operation, an increased PN production rate was observed with longer resting times. As discussed above, TBA ions are not attracted electrostatically by the negatively charged electrode during resting times, and variations on the TBA ion concentration in the EDL could affect water coverage of the electrode surface and molecule solvation in the EDL. If the TBA concentration in the EDL changes, molecule solvation and water coverage would vary, together with the product distribution of the reaction. Independently of the migration of TBA ions, longer resting times can increase AN concentration in the EDL, which would also increase production of AN-derived molecules, including PN and ADN. The results obtained thus suggest that the dependence of PN formation on AN concentration is stronger than that of ADN formation on reactant concentration.

Figure 6:
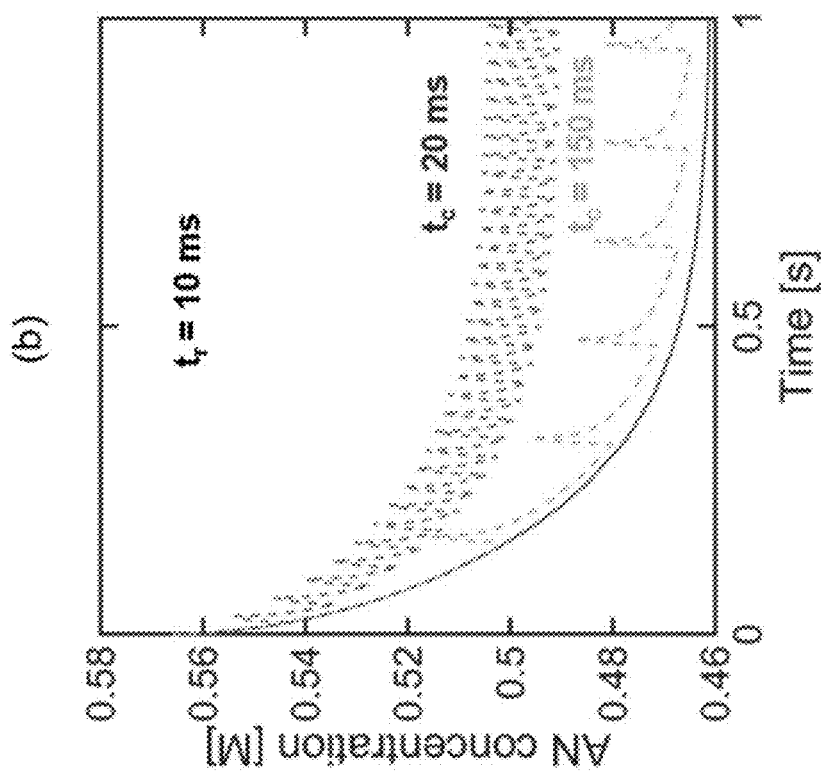
FIG. 6 shows examples of the effect of (a) resting time and (b) cathodic time on the simulated time-dependent reactant concentration at the electrode surface at −60 mA cm$^{-2}$ cathodic current and 0 mA cm$^{-2}$ resting current. The solid blue line describes the concentration profile under DC conditions at −60 mA cm$^{-2}$. Initial bulk AN concentration is fixed at 0.6 M and only diffusion-based reactant replenishment is considered in the model.
Figure 6:
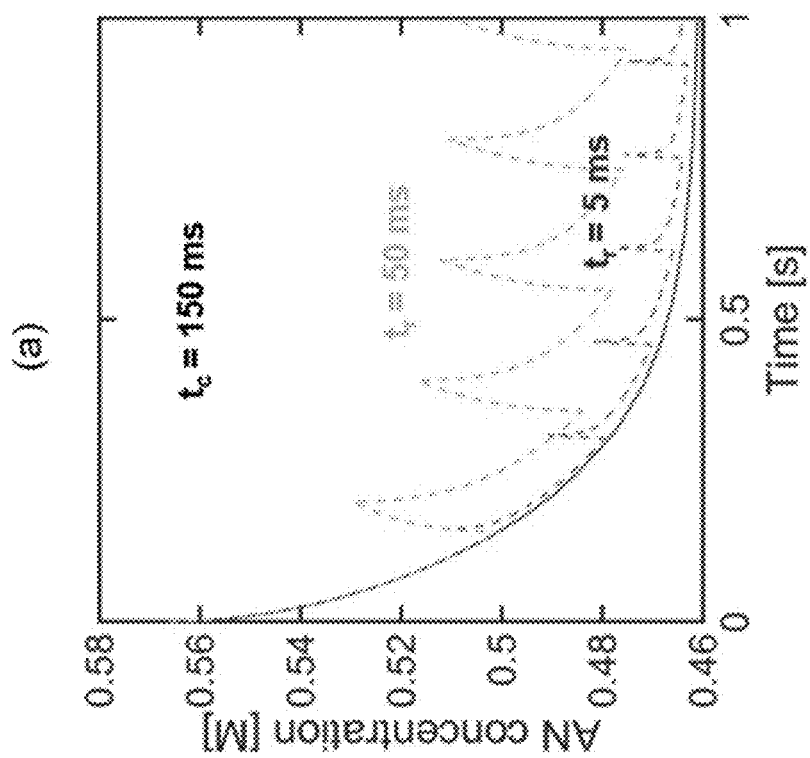

As observed on FIG. 6 (b), AN concentration in the EDL decreases with increasing cathodic time, given the longer reactant consumption, which explains the increase in PN concentration observed. Optimizing the cathodic time therefore requires a tradeoff between the control of mass transport limitations and an overall cathodic time that maintains ADN production rates. FIG. 5 (a) shows that the strategic control of the concentration profile of reactant and electrolyte species next to the electrode surface can lead to higher ADN production rates (up to 20% increase in ADN production) with lower energy inputs when compared to DC operation.

Effect of cathodic potential. As portrayed in FIG. 4, the cathodic potential implemented and its corresponding current density determine (i) the reaction rate and electron flux, together with the extent of mass transport limitations in the system, and (ii) the electrostatic interaction between the electrode and charged electrolyte species. Given that the concentration profile of reactant and electrolyte species will vary with the cathodic potential, the optimum combination of resting and cathodic times is expected to change as well.

Figure 7:
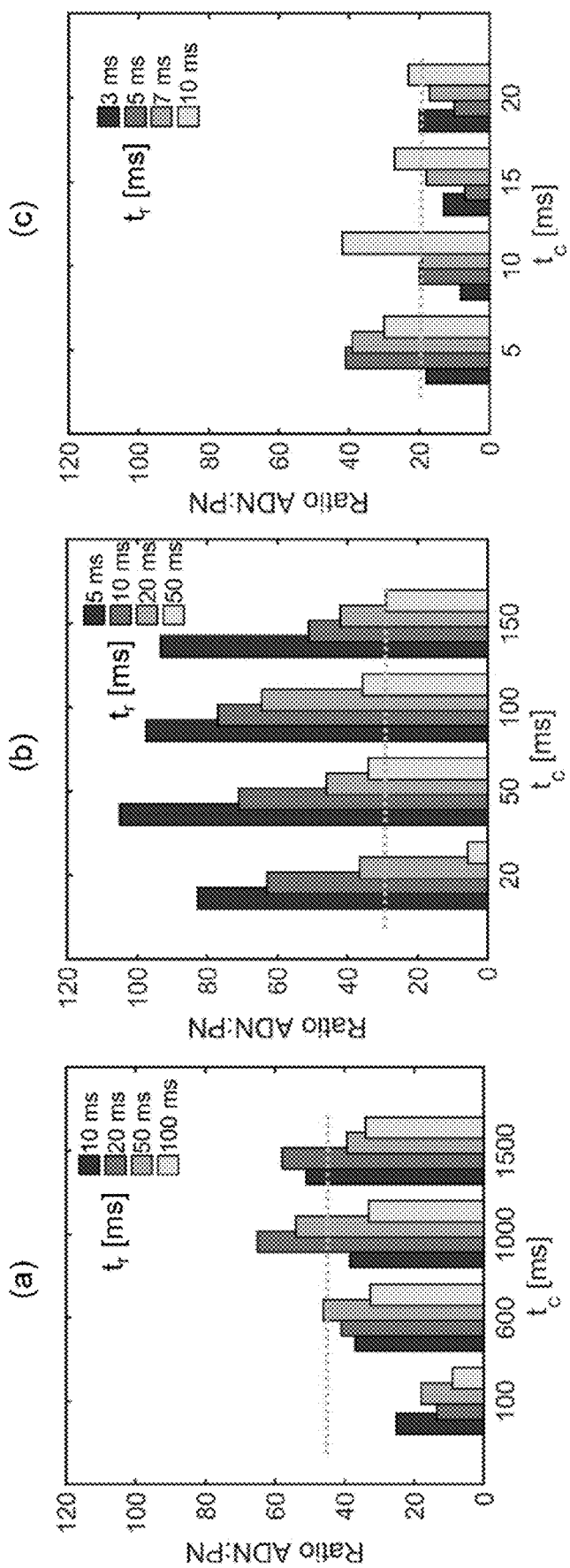
FIG. 7 shows an example of ADN:PN production ratio at (a) −2.5 V, (b) −3.5 V, and (c) −4.5 V vs Ag/AgCl cathodic potentials for various $t_r$ and $t_c$ combinations with <4% standard deviation. Resting potential is maintained at 0 V vs Ag/AgCl reference electrode. The dotted lines represent the ADN:PN ratio obtained under DC operation at −2.5 V, −3.5 V, and −4.5 V vs Ag/AgCl respectively. Moving from left to right on the $t_c$ axis, the values for each of the four $t_c$ times corresponds to a $t_r$ of 5 ms, 10 ms, 20 ms, and 50 ms.

FIG. 7 shows the ADN:PN production ratio for (a) −2.5 V, (b) −3.5 V, and (c) −4.5 V vs Ag/AgCl cathodic potential, corresponding to −30 mA cm$^{-2}$, −60 mA cm$^{-2}$, and −90 mA cm$^{-2}$ approximately. The ratio obtained under chronoamperometric conditions (dotted lines) decreases with increasing electrode potential, which is in agreement with the expected increased PN production under mass transport limitations.

Figure 8:
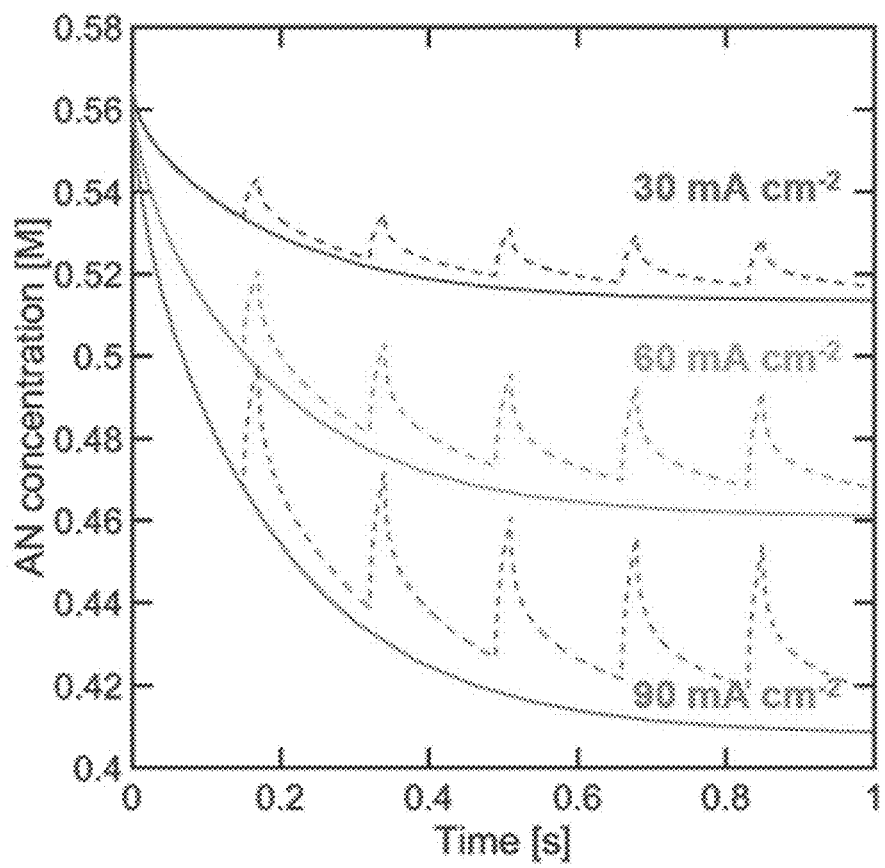
FIG. 8 shows an example of the effect of cathodic potential/current density on the simulated time-dependent reactant concentration at the electrode surface with 150 ms cathodic time and 10 ms resting time. The solid lines describe the concentration profile under DC operation and the dotted lines correspond to the concentration profile under pulsed electrolysis. Initial bulk AN concentration is fixed at 0.6 M and only diffusion-based reactant replenishment is considered in the model.

As would be expected, the time scales used for cathodic and resting periods that maximize the ADN:PN ratio depend on the cathodic potential. Although the previous section showed that longer cathodic times can bolster PN formation due to mass transport limitations at −3.5 V vs Ag/AgCl, optimum ADN:PN ratios were obtained with much longer pulses at −2.5 V vs Ag/AgCl. The use of lower cathodic potentials limits the electron flux, allowing the use of longer cathodic pulses before reaching reactant depletion. FIG. 8 presents the simulated reactant concentration at the electrode surface at various current densities, showing a faster reactant depletion with higher current densities. The reactant concentration profiles vary according to the cathodic potential, and within any cathodic potential they will be influenced by the pulse duration, as discussed on FIG. 6. In this way, in order to effectively enhance ADN over PN production, it was necessary to use shorter resting times with higher electrode potential, with the goal of optimizing the concentration profile of species in the EDL Interestingly enough, the highest increase in ADN:PN ratio with respect to DC operation was found at −3.5 V vs Ag/AgCl, suggesting that the effectiveness of reactant concentration regeneration and mitigation of mass transport limitations in the system depends on the cathodic reaction rate. Above this value, when the cathodic potential reaches −4.5 V vs Ag/AgCl, pulsed electrolysis can help improve the ADN:PN ratio, however ADN production is limited by the short cathodic times and mass transport limitations are not completely overcome with diffusion-based reactant concentration regeneration. Furthermore, within any cathodic potential, a maximum in ADN:PN ratio can be found at different combinations of $t_c$ and $t_r$, tailored to the magnitude of the mass transport limitations present.

Effect of resting potential. The previous results show the effects of the dynamic dosing of electrons with cathodic potential and pulse duration, but the resting potential has been maintained at 0 V vs Ag/AgCl. This corresponds to +0.859 V vs SHE, eliminating all possibility of reactant reduction during resting times. FIG. 8 displays the effect that resting electrode potential can have on product distribution, studying the possibility to further increase ADN:PN ratio with resting potentials that are lower than −3.5 V (fixed cathodic potential). In this case, electrons are injected during resting times, yet their flux is limited by a lower reaction rate tied to a lower current density imposed.

Considerable variations are observed on ADN production rate and ADN:PN ratio with resting potential. ADN:PN ratio is mostly higher with 0 V vs Ag/AgCl resting potential, suggesting that the uninterrupted electron flow can generate concentration profiles in the EDL that are not optimum for ADN formation. As reported in other studies, the electrode can undergo surface modifications when oxidation potentials are applied. Surface morphology changes could affect the affinity and binding energy of intermediate species with the electrode surface, thus altering product distribution.

Figure 9:
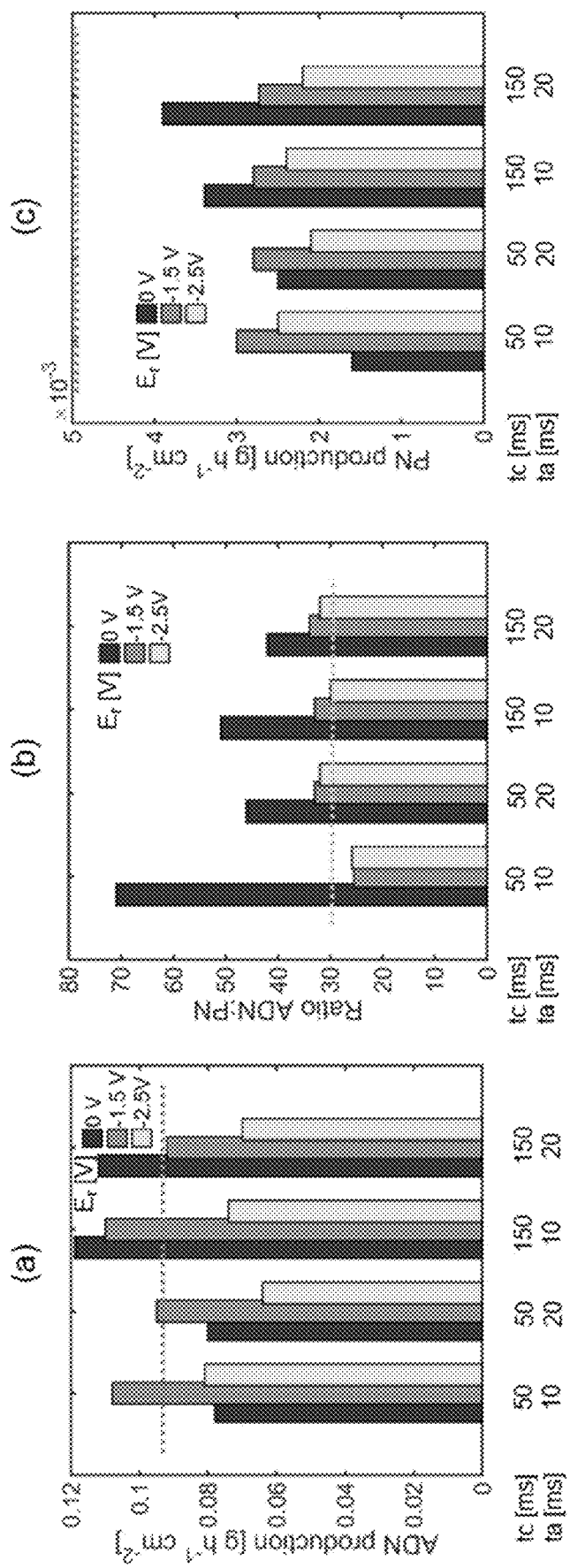
FIG. 9 shows an example of the effect of resting electrode potential on the (a) ADN production rate, (b) ADN:PN ratio, and (c) PN production rate at various $t_c$ and $t_r$ combinations with <2% standard deviation. Cathodic potential was maintained at −3.5 V vs Ag/AgCl in all cases and the dotted lines correspond to operation under chronoamperometric conditions.

FIG. 9 indicates that the strategic combination of $t_r$, $t_c$, $E_r$, and $E_c$ is essential to maintain the ADN production rate. However, independently of the resting potential, pulses appear to effectively mitigate mass transport limitations with reactant concentration replenishment, leading to a significantly reduced PN production rate (FIG. 9).

Machine learning and pulsed electrolysis. The study of the effect of $t_r$, $t_c$, $E_r$, and $E_c$ on product distribution and production rates reveals the complexity of processes that take place in the EDL and the difficulty to individually study the nearly unlimited number of possibilities for parameter combinations and how they affect performance metrics. The results obtained suggest that the effect of pulsed potentials on reactant concentration in the EDL is not enough to explain the behavior observed on reaction selectivity. Ion migration, molecule solvation, electrode surface modification, and overall cathodic time are defined by $t_r$, $t_c$, $E_r$, and $E_c$, and have a strong influence on production rates. The development of ANN that can predict ADN and PN production rates taking combinations of the aforementioned parameters would allow the quick and accurate evaluation of the advantages of pulsed electrolysis, determining the optimum parameters to maximize reaction performance and would help develop a deeper understanding of the nano-scale processes taking place.

Figure 10:
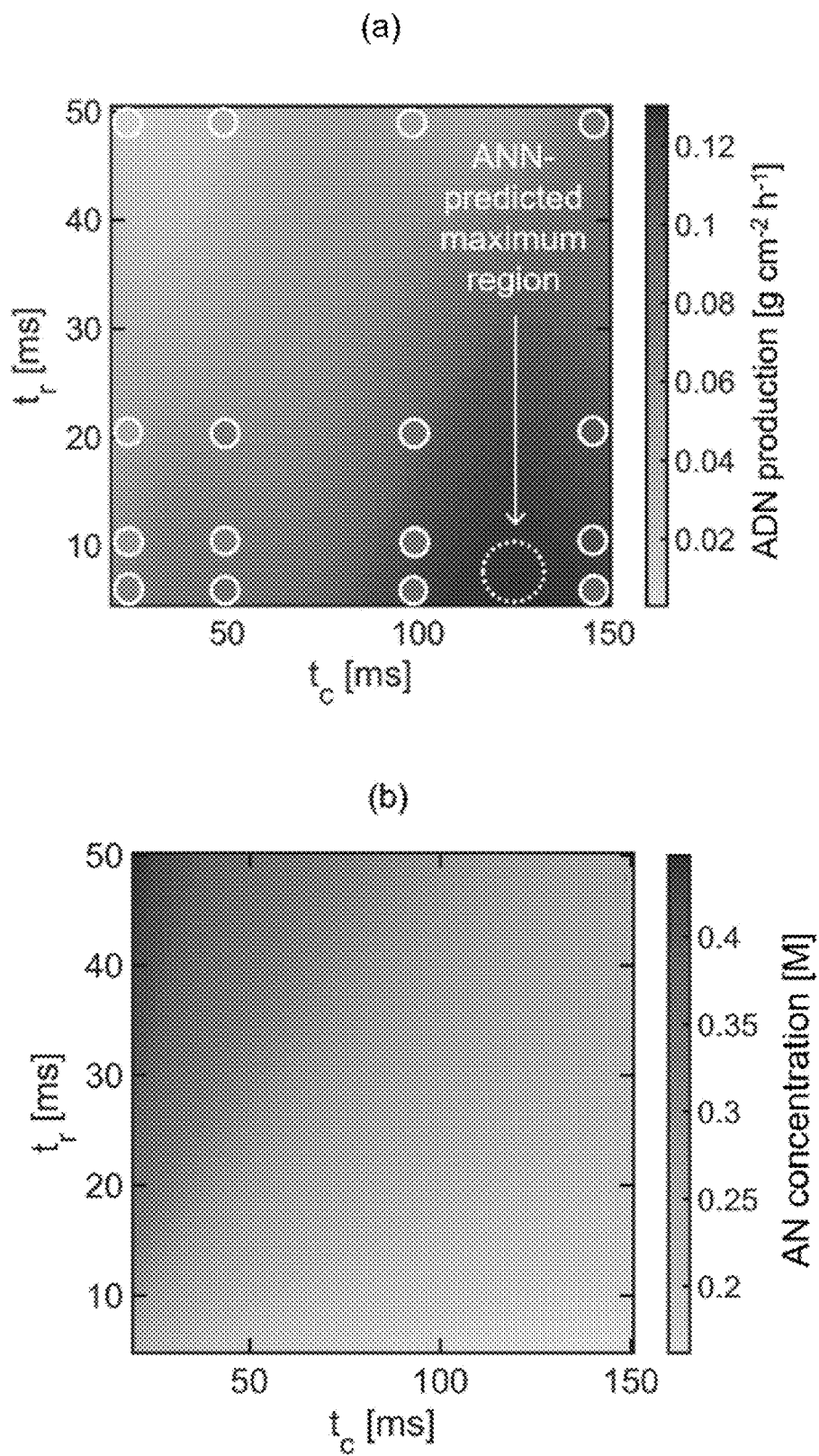
FIG. 10 shows (a) prediction of ADN production with an ANN using $t_r$ and $t_c$ as inputs. A production error of 10% is observed within the frame and 25% on the edges. (b) Simulated AN average steady state concentration at the electrode surface under pulsed electrolysis.

FIG. 10(*a*) presents an ANN generated with $t_r$ and $t_c$ as inputs, trained with the data collected experimentally to predict ADN production with 10% error within the frame and 25% error on the edges. The number of inputs and prediction accuracy can be further improved with the addition of data points that help effectively train the neural network. This representation as it is can already help identify the ranges that maximize (highest $t_c$ and intermediate $t_r$) or minimize (lowest $t_c$ and highest $t_r$) ADN production. This data can be complemented with the simulated AN average steady state concentration at the electrode surface with pulsed potentials, shown on FIG. 9 (*b*). The results suggest that ADN production is maximized at an intermediate reactant concentration, preventing PN formation (low AN concentration) or self-polymerization (high AN concentration). The fact that the trend observed for ADN production does not correspond completely to the AN concentration profile supports the statement that the control of reactant concentration in the EDL can help effectively mitigate PN formation but is only one of the factors that can strongly affect ADN production.

The results elucidate the advantages and the promise of pulsed electrolysis in organic electrosynthesis, using the electrohydrodimerization of acrylonitrile to adiponitrile as an example reaction. Organic systems commonly face challenges with mass transport limitations due to the low solubility of organic molecules in aqueous media, and this is evidenced in the electrosynthesis of ADN with an increased PN production rate. As shown in this Example, electrochemical pulsed techniques can be used to help control reactant concentration in the EDL through diffusion-based replenishment from the bulk, effectively limiting PN production. Furthermore, electrochemical pulses appear to influence several complex processes in the EDL, including reactant replenishment, ion migration, molecule solvation and binding energies after surface modifications. Although PN formation was mitigated in most cases, a careful control of pulse amplitude and duration is essential to regulate these processes and maintain optimum concentration profiles for the species involved in the EDL. Cathodic times need to be further optimized to balance the tradeoff between mass transport limitations at longer $t_c$ in order to maximize ADN production over other reaction by-products.

Cathodic times and cathodic potential were the most influencing factors on ADN production, and the optimization of the parameters studied led to a 20% increase in ADN production, with respect to the case of DC operation, together with a 6% reduction in energy input. This was obtained with −3.5V vs Ag/AgCl cathodic potential, 0 V vs Ag/AgCl resting potential, 150 ms cathodic time, and 10 ms resting time.

With a nearly unlimited number of possibilities for combination of operation parameters, machine learning principles become a powerful tool to improve the understanding of the nano-scale process governing mass transport in the EDL. Furthermore, artificial neural networks can be built to predict reaction performance within a continuous landscape of parameters although only several discrete points have been experimentally measured. With this mindset, inline characterization and electrochemical flow systems can be designed to collect performance data in a continuous and expedite manner, which will be fed into ANNs to predict an unlimited amount of additional points, allowing the identification of reaction parameters and conditions that maximize reaction performance.

Although the present disclosure has been described with respect to one or more particular embodiments and/or examples, it will be understood that other embodiments and/or examples of the present disclosure may be made without departing from the scope of the present disclosure.

The invention claimed is:

1. An electrohydrodimerization method for making one or more aliphatic compound comprising two or more electron withdrawing groups comprising:
electrolyzing a reaction mixture comprising:
one or more aliphatic olefinic compound comprising one or more electron withdrawing group;
one or more salts; and
water;
wherein the reaction mixture has at least an initial pH of 7 to 13,
wherein the reaction mixture is in contact with a cathode having for a selected duration at least one cathode potential sufficient to hydrodimerize the one or more aliphatic olefinic compound comprising one or more electron withdrawing group and for at least one other selected duration a higher cathode potential at which the hydrodimerization of the one or more aliphatic olefinic compound comprising one or more electron withdrawing group occurs at a slower rate or is completely suppressed, and the electrolysis is carried out using a pulsed potential waveform applied to the cathode, and
wherein the one or more aliphatic compound comprising two or more electron withdrawing groups is formed.

2. The method of claim 1, wherein the pulsed potential waveform has a base (resting) potential selected within a range where no faradaic reaction occurs or occurs at a lower rate than during the cathodic potential and at least one cathodic (pulse) potential.

3. The method of claim 2, wherein the base potential is applied for a resting duration of less than 50 ms and the cathodic potential is applied for a cathodic duration of from 5 ms to 2000 ms.

4. The method of claim 3, wherein each resting duration is the same as each other resting duration and/or each cathodic duration is the same as each other cathodic duration.

5. The method of claim 2, wherein the pulsed potential waveform alternates between the base potential and the cathodic potential.

6. The method of claim 2, wherein each instance of base potential has a same potential value as each other instance of the base potential and/or each instance of the cathodic potential has a same potential value as each other instance of the cathodic potential.

7. The method of claim 2, wherein each base potential is the same or varies in the range of 0 V to −4 V measured against a Ag/AgCl reference electrode and/or the cathodic potential is equal to or lower than −2 V.

8. The method of claim 2, wherein the base potential of a pulse is constant throughout the resting duration and/or the cathodic potential of a pulse is constant throughout the cathodic duration.

9. The method of claim 2, wherein the base potential of a pulse varies during the resting duration and/or the cathodic potential of a pulse varies during the cathodic duration.

10. The method of claim 9, wherein the base potential of a pulse varies during the resting duration and the cathodic potential of a pulse varies during the cathodic duration.

11. The method of claim 1, wherein the one or more aliphatic olefinic compound is at least initially present in the reaction at a concentration of 3 to 30 wt % (based on the total weight of the reaction mixture).

12. The method of claim 1, wherein the one or more salts are chosen from buffer salts, EDTA, chelating agents, ion-orienting quaternary ammonium salts, and combinations thereof.

13. The method of claim 1, wherein the one or more salts are at least initially present in the reaction at a concentration of 0.1 to 15 wt % (based on the total weight of the reaction mixture).

14. The method of claim 1, wherein the one or more aliphatic olefinic compound concentration and/or salt concentration and/or pH is constant or changes as a function of time.

15. The method of claim 1, wherein the electrolysis is carried out in an electrochemical cell comprising a cathode.

16. The method of claim 15, wherein the electrochemical cell further comprises a metal anode and, optionally, a reference electrode.

17. The method of claim 15, wherein the electrochemical cell further comprises a separator.

18. The method of claim 15, wherein the cathode has an electrochemically available surface comprising a metal, a carbon, or a combination thereof.

19. The method of claim 1, further comprising separation at least a portion of, substantially all, or all of the one or more aliphatic compound comprising two or more electron withdrawing groups from the reaction mixture.

* * * * *